(12) United States Patent
Blanes Mira et al.

(10) Patent No.: US 7,473,679 B2
(45) Date of Patent: Jan. 6, 2009

(54) TREATMENTS EMPLOYING NEURONAL EXOCYTOSIS-INHIBITING PEPTIDES

(75) Inventors: Ma Clara Blanes Mira, Hospitalet de Llobregrat (ES); Ma Mercedes Llobregat Hernandez, Hospitalet de Llobregrat (ES); Ana Isabel Gil Tebar, Hospitalet de Llobregrat (ES); Gregorio Joaquin Fernandez Ballester, Hospitalet de Llobregrat (ES); Rosa Ma Planell Cases, Hospitalet de Llobregrat (ES); Antonio Vicente Ferrer Montiel, Hospitalet de Llobregrat (ES); Salvador Viniegra Bover, Hospitalet de Llobregrat (ES); Luis Miguel Gutierrez Perez, Hospitalet de Llobregrat (ES); Teresa Carbonell Castello, Hospitalet de Llobregrat (ES); Enrique Perez Paya, Hospitalet de Llobregrat (ES)

(73) Assignee: Lipotec, S.A., Hospitalet de Llobregat (ES)

( * ) Notice: Subject to any disclaimer, the term of this patent is extended or adjusted under 35 U.S.C. 154(b) by 0 days.

(21) Appl. No.: 11/327,952

(22) Filed: Jan. 9, 2006

(65) Prior Publication Data
US 2006/0276392 A1    Dec. 7, 2006

Related U.S. Application Data

(62) Division of application No. 10/030,485, filed as application No. PCT/ES00/00058 on Feb. 18, 2000, now Pat. No. 7,015,192.

(30) Foreign Application Priority Data
Apr. 23, 1999    (ES)    .................................. 9900844

(51) Int. Cl.
*A61K 38/00*    (2006.01)
*C07K 14/00*    (2006.01)

(52) U.S. Cl. ............................. 514/2; 514/13; 514/14; 530/300; 530/334; 530/344; 435/69.1; 435/7.1; 424/9.1

(58) Field of Classification Search .................... 514/2, 514/13, 14; 530/300, 334, 344; 435/69.1, 435/7.1, 9.1
See application file for complete search history.

(56) References Cited

OTHER PUBLICATIONS

Shorr et al., "The Use of Botulinum Toxin in Blepharospasm," *American Journal of Ophthalmology*, 99:542-546 (May 1985).
Jankovic, "Botulinum A Toxin in the Treatment of Blepharospasm," *Advances in Neurology*, vol. 49:467-472 (1988).
Elston et al., "Treatment of strabismus in adults with botulinum toxin A," *British Journal of Ophthalmology*, 69:718-724 (1985).
Blitzer et al., "Botulinum Toxin Injection for the Treatment of Oromandibular Dystonia," *Ann. Otol. Rinol. Larvngol.*, 98:93-97 (1989).
Jankovic et al., "Botulinum A toxin for cranial-cervical dystonia: A double-blind, placebo-controlled study," *Neurology*, 37:616-623 (1987).
Ferguson, "Cephalometric interpretation and assessment of facial asymmetry secondary to congenital torticollis," *Int. J. Oral Maxilofac. Surg.*, 22:7-10 (1993).
Jankovic, "Botulinum Toxin in the Treatment of Dystonic Tics," *Movement Disorders*, 9(3):347-349 (1994).
Bushara, "Sialorrhea in amyotrophic lateral sclerosis: a hypothesis of a new treatment—botulinum toxin A injections of the parotid glands," *Medical Hypotheses*, 48:337-339 (1997).
Borg-Stein et al., "Botulinum Toxin for the Treatment of Spasticity in Multiple Sclerosis," *Am. J. Phys. Med. Rehabil.*, 72:364-368 (1993).
Blasi et al., "Botulinum neurotoxin A selectively cleaves the synaptic protein SNAP-25," *Nature*, 365:160-163 (Sep. 9, 1993).
Südhof, "The synaptic vesicle cycle: a cascade of protein interactions," *Nature*, 375:645-653 (Jun. 22, 1995).
Gutierrez et al., "A Peptide That Mimics the C-terminal Sequence of SNAP-25 Inhibits Secretory Vesicle Docking in Chromaffin Cells," *J. Biol. Chem.*, 272(5):2634-39 (1997).
Monyer et al., "Oxygen or Glucose Deprivation-Induced Neuronal Injury in Cortical Cell Cultures is Reduced by Tetanus Toxin," *Neuron*, 8:967-973 (May 1992).
Simpson, "Molecular Pharmacology of Botulinum Toxin and Tetanus Toxin," *Ann. Rev. Pharmacol. Toxicol.*, 26:427-453 (1986).
Montecucco et al., "Tetanus and botulism and neurotoxins: a new group of zinc proteases," *Trends Biol. Sci.*, 18:324-327 (1993).
Lipton et al., "Excitatory Amino Acids as a Final Common Pathway for Neurologic Disorders," *Mechanisms of Disease*, 330(9):613-622 (1994).
Bigalke et al., "Tetanus Toxin and Botulinum A Toxin Inhibit Release and Uptake of Various Transmitters, as Studied with Particulate Preparations from Rat Brain and Spinal Cord," *Naunyn-Schmeideberg's Arch. Pharmacol.*, 316:244-251 (1981).
Habermann et al., "Tetanus Toxin and Botulinum A and C Neurotoxins Inhibit Noradrenaline Release from Cultured Mouse Brain," *Journal of Neurochemistry*, 51:522-527 (1988).
Habermann, "Inhibition by tetanus and botulinum A toxin of the release of [$^3$H]noradrenaline and [$^3$H]GABA from rat brain homogenate," *Experientia*, 44:224-226 (1988).

*Primary Examiner*—Chih-Min Kam
(74) *Attorney, Agent, or Firm*—Intellectual Property Law Group LLP; Otto O. Lee; Juneko Jackson

(57) ABSTRACT

The peptide has a sequence of 3 to 30 adjacent amino acids from the amino end of protein SNAP-25 and is useful as neuronal exocytosis inhibitor. The cosmetic and pharmaceutical compositions contain said peptide and optionally one or more peptides from the carboxyl end of SNAP-25. The compositions are suitable for the treatment of facial wrinkles, asymmetry and pathological neuronal exocytosis-mediated pathological disorders and alterations.

10 Claims, No Drawings

SEQUENCE LISTING

```
<160> NUMBER OF SEQ ID NOS: 6

<210> SEQ ID NO 1
<211> LENGTH: 82
<212> TYPE: PRT
<213> ORGANISM: Artificial Sequence
<220> FEATURE:
<223> OTHER INFORMATION: Description of Artificial Sequence: Amino end
      of protein SNAP 25

<400> SEQUENCE: 1

Ala Glu Asp Ala Asp Met Arg Asn Glu Leu Glu Glu Met Gln Arg Arg
 1               5                  10                  15

Ala Asp Gln Leu Ala Asp Glu Ser Leu Glu Ser Thr Arg Arg Met Leu
                20                  25                  30

Gln Leu Val Glu Glu Ser Lys Asp Ala Ile Arg Thr Leu Val Met Leu
            35                  40                  45

Asp Glu Gln Gly Glu Gln Leu Glu Arg Ile Glu Glu Gly Met Asp Gln
        50                  55                  60

Ile Asn Lys Asp Met Lys Glu Ala Glu Lys Asn Leu Thr Asp Leu Gly
65                  70                  75                  80

Lys Phe

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Glu Met Gln Arg Arg
 1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 3

Glu Leu Glu Glu Met Gln Arg Arg Ala Asp Gln Leu Ala
1               5                   10

<210> SEQ ID NO 4
<211> LENGTH: 86
<212> TYPE: PRT
<213> ORGANISM: Artificial Sequence
<220> FEATURE:
<223> OTHER INFORMATION: Description of Artificial Sequence: Carboxyl
      end of SNAP-25

<400> SEQUENCE: 4

Val Asp Glu Arg Glu Gln Met Ala Ile Ser Gly Gly Phe Ile Arg Arg
1               5                   10                  15

Val Thr Asn Ala Arg Glu Asn Glu Glu Met Asp Glu Asn Leu Glu Gln
            20                  25                  30

Val Ser Gly Ile Leu Gly Asn Leu Arg His Met Ala Leu Asp Met Gly
        35                  40                  45

Asn Glu Ile Asp Thr Gln Asn Arg Gln Ile Asp Arg Ile Met Glu Lys
    50                  55                  60

Ala Asp Ser Asn Lys Thr Arg Ile Asp Glu Ala Asn Gln Arg Ala Thr
65                  70                  75                  80

Lys Met Leu Gly Ser Gly
                85

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ile Met Glu Lys Ala Asp Ser Asn Lys Thr Arg Ile Asp Glu Ala
1               5                   10                  15

Asn Gln

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Asp Ser Asn Lys Thr Arg Ile Asp Glu Ala Asn Gln Arg Ala Thr
1               5                   10                  15

Lys Met Leu
```

TREATMENTS EMPLOYING NEURONAL EXOCYTOSIS-INHIBITING PEPTIDES

CROSS-REFERENCE TO RELATED APPLICATION

This application is a divisional of U.S. application Ser. No. 10/030,485, filed Jun. 27, 2002, now U.S. Pat. No. 7,015,192, which is a 371 of PCT/ES00/00058, filed Feb. 18, 2000, the entire disclosure of which application is hereby incorporated herein by reference thereto.

FIELD OF THE INVENTION

This invention refers to peptides derived from the amino end of protein SNAP-25, useful as inhibitors of neuronal exocytosis, and to their use in cosmetic and/or therapeutic applications, together (optionally) with a peptide derived from the carboxyl end of protein SNAP-25

BACKGROUND OF THE INVENTION

The basis or mechanism for the formation of facial wrinkles is the tensing of the muscles of the epidermis that drag the skin inwards. This muscular tension is the result of hyperactivity of the nerves innervating the facial muscles. Nerve hyperactivity is characterized by the uncontrolled and excessive release of neurotransmitters that excite muscle fibers. Because of this, the molecules that control neuronal exocytosis contribute to relaxing muscular tension, and consequently, to eliminating wrinkles.

*Botulinum* toxins are a family of bacterial neurotoxins produced by *Clostridium Botulinum* (1) [see section regarding BIBLIOGRAPHY]. 7 different serotypes are known (serotypes A, B, C, D, E, F and G) with an average molecular weight of 150 kDa. These toxins inhibit acetylcholine exocytosis in the neuromuscular junction (nerve-muscle synapse) of the skeletal muscle (1).

At a molecular level, *botulinum* toxins are proteases that degrade neuronal proteins involved in the exocytosis mechanism activated by the calcium ion (1-3). For example, *botulinum* toxin A, the one most commonly used clinically and cosmetically [because of its applications in eliminating facial wrinkles and asymmetry, and to mitigate the symptomatology of spastic diseases], cleaves the neuronal protein SNAP-25. This protein (SNAP-25) plays a key role in neurosecretion, as it is involved in the formation of a protein complex (known as SNARE complex or fusion complex), which directs and controls the release of acetylcholine accumulated in vesicles. The nucleus of said fusion complex is made up of proteins SNAP-25 and syntaxin, located in the presynaptic plasma membrane, and protein synaptobrevin (or VAMP), located in the vesicular plasma membrane (4, 5). The main function of the fusion complex is to bring the vesicle loaded with neurotransmitter (acetylcholine) nearer to the presynaptic plasma membrane and put it in contact with same (4, 5). In this way, in response to an elevated concentration of calcium, the fusion of both plasma membranes is encouraged, thus producing the release of the neurotransmitter. Therefore, said vesicle docking and fusion protein complex (SNARE) is a key target in controlling neurosecretion. Cleaving any of the proteins that make up the fusion complex prevents its assembly, and therefore inhibits vesicle release and neuronal exocytosis.

The power of *botulinum* toxins and, in particular, serotype A (BOTOX®) to inhibit neurosecretion, as well as their neuronal selectivity (they only act on neurons) is being widely used therapeutically to correct spastic ailments such as dystonias, strabismus, tics, blepharospasm, facial scoliosis, etc. (6-13). *botulinum* toxin A (*botulinum* A) is, moreover, an effective agent for eliminating facial wrinkles and asymmetry. In fact, the administration of BOTOX® is the first effective non-surgical therapy to eliminate the signs of aging (6, 7).

Therapeutic and cosmetic treatment with BOTOX® consists of a localized injection of diluted pharmaceutical preparations (*botulinum* A-hemagglutinin complex, 500 kDa) in the areas where muscular tension is localized. The paralytic effects of the toxin are reversible with an average duration of 6 months (6, 7). The treatment, therefore, requires repeated injections of BOTOX®. The main problem with this treatment is the chance that it may trigger an immune reaction against the pharmaceutical preparation due to the fact that, because of its molecular size, it may be recognized by the patient's immune system. The appearance of antibodies against *botulinum* A is a serious problem, as it contributes to a clear decrease in the treatment's effectiveness (6-13). This loss of effectiveness in treatment with BOTOX® means the need to increase the preparation's concentration level in later treatments, which in turn produces a potentiation of the immune response. As an alternative, the use of different *botulinum* toxin (BoTox) serotypes has been discussed, such as BoTox B, BoTox F and BoTox E. Nevertheless, the application of pharmaceutical preparations with different serotypes cannot be considered a solution to the problem, as sooner or later the immune reaction may once again occur. In addition, treatment with *botulinum* toxins is expensive, mainly because of the lability and instability of the pharmaceutical preparations containing them.

There is, therefore, a pressing need to develop molecules that imitate the paralytic effects of the *botulinum* toxins, but with much simpler and more stable molecular structures, which do not cause immune reactions, and whose manufacturing cost is economical. Peptide-type molecules comply with these properties.

Amino acid sequences that inhibit neuronal exocytosis have been described. Specifically, it has been proven that peptides with more than 20 amino acids, deriving from the C-terminal sequence of SNAP-25, block the release of catecholamines from permeabilized chromaffin cells (14). Likewise, peptides deriving from the amino acid sequences of proteins syntaxin and VAMP have been described that can also affect the exocytotic process (15). Although these peptides show biological activity, their later development as cosmetic and/or therapeutic agents has not occurred, most likely due to their size, as this complicates their development as useful therapeutic agents and makes it more expensive. Therefore, there is a need to find molecules of a smaller size that can be applied in cosmetics and medicine.

This invention provides a solution to the existing needs which includes the discovery of smaller amino acid sequences, between 3 and 30 amino acids, deriving from the amino end (N-terminal domain) of protein SNAP-25, which inhibit neuronal exocytosis. In addition, it has been discovered that the simultaneous use of peptides deriving from the amino end and from the carboxyl end (C-terminal domain) of SNAP-25 produces a considerable increase in their inhibitory activity, i.e., there is a potentiation of their activity compared to that shown by individual peptides.

Therefore, one object of this invention is a peptide that has a sequence made up of 3 to 30 adjacent amino acids contained on the amino end of protein SNAP-25, which inhibits neuronal exocytosis.

An additional object of this invention is a nucleic acid that essentially codes for one of the peptides provided by this invention. The plasmids and vectors that contain said nucleic acid (also identified as constructions), as well as the cells transformed with said plasmids or vectors that express a peptide of the invention, also constitute additional objects of this invention.

Another additional object of this invention is a mixture of at least one of the peptides provided by this invention and at least one peptide that has a sequence made up of 3 to 30 adjacent amino acids contained on the carboxyl end of protein SNAP-25.

Another additional object of this invention is a cosmetic composition that includes at least one of the peptides provided by this invention. The use of the peptides provided by this invention in the preparation of said cosmetic composition, as well as the method of cosmetic treatment that includes the application of said cosmetic composition, constitute additional objects of this invention.

Another additional object of this invention is a pharmaceutical composition that includes at least one of the peptides provided by this invention, or alternatively, a vector containing a nucleic acid that codes for one of the peptides of the invention. The use of the peptides and vectors (constructions) provided by this invention in the preparation of said pharmaceutical compositions, as well as the method of treating humans or animals encompassed by the application of said cosmetic composition, constitute additional objects of this invention.

Another additional object of this invention is a combination of drugs that includes at least one of the peptides provided by this invention, along with, at least, one drug intended for a second therapeutic target which may be the same as or different from the therapeutic target at which the peptide provided by this invention is aimed.

DETAILED DESCRIPTION OF THE INVENTION

This invention provides a peptide deriving from the amino end of protein SNAP-25. More specifically, the invention provides a peptide, henceforth known as the peptide of the invention, which has a sequence of 3 to 30 adjacent amino acids contained in SEQ. ID. No. 1 [see the section regarding the SEQUENCE LIST].

The invention also includes peptides which are substantially homologous to the peptide of the invention. In the sense used in this description, the expression "substantially homologous" means that the peptide in question has a homology level, as far as amino acids are concerned, of at least 60%, and preferably of at least 80%, and even more preferably, of at least 95%.

The invention also includes peptides which are functionally equivalent to the peptide of the invention. In the sense used in this description, the expression "functionally equivalent" means that the peptide in question has at least one of the biological activities of the peptide of the invention, such as, for example, the ability to at least partially inhibit neuronal exocytosis.

In one particular embodiment, the peptide of the invention has a length of 3 to 20 amino acids, and preferably from 6 to 19 amino acids.

The amino acids that make up the structural units of the peptide of the invention may have D- or L-configuration. The amino acid from the amino end may have an acetylated terminal amino group, and the amino acid from the carboxyl end may have an amidated terminal carboxyl group. Therefore, this invention also includes derivatives of the peptide of the invention in which the amino-terminal end is acetylated and/or in those where the carboxy-terminal end is amidated.

Particular examples of peptides of the invention are those peptides that have sequences of amino acids shown in SEQ. ID No. 2 and SEQ. ID No. 3.

Within the scope of this invention are cosmetically and/or pharmaceutically acceptable salts of the peptide of the invention. The term "cosmetically and/or pharmaceutically acceptable salts" includes salts customarily used to form metal salts or salts' formed by adding free acids or bases. The nature of the salt is not critical, as long as it is cosmetically and/or pharmaceutically acceptable. Cosmetically and/or pharmaceutically acceptable salts of the peptide of the invention may be obtained from acids or bases, organic or inorganic, by conventional methods which are well known to technicians in these matters, by making the appropriate acid or base react with the peptide of the invention.

In addition, the peptide of the invention may undergo reversible chemical modifications in order to increase its bioavailability (including stability and fat solubility) and its ease in passing through the blood-brain barrier and epithelial tissue. Examples of such reversible chemical modifications include the esterification of the carboxylate groups of glutamic and aspartic amino acids with an acetyl-methyl group, by which the negative charge of the amino acid is eliminated and its hydrophobicity is increased. This esterification is reversible, as the ester link formed is recognized by intracellular esterases which hydrolyze it, giving back the charge to the aspartic and glutamic residues. The net effect is an accumulation of intracellular peptide, as the internalized, de-esterified peptide cannot cross the cell membrane.

The peptide of the invention can be obtained through conventional methods for solid-phase chemical peptide synthesis, following Fmoc and/or Boc-based methodology (16).

Alternatively, the peptide of the invention can be obtained through conventional methods based on recombinant DNA technology, e.g., through a method that, in brief, includes inserting the nucleic acid sequence that codes for the peptide of the invention into an appropriate plasmid or vector, transforming competent cells for said plasmid or vector, and growing said cells under conditions that allow the expression of the peptide of the invention and, if desired, isolating and (optionally) purifying the peptide of the invention through conventional means known to experts in these matters. The nucleic acid sequence that codes for the peptide of the invention may be easily deduced from the correspondence that exists between the amino acids and the nucleotide codons that code for such amino acids. In this case, an additional object of the invention is an isolated nucleic acid sequence that codes for the peptide of the invention. In one particular embodiment, said nucleic acid is selected among single-strand DNA, double-stranded DNA, and RNA. Additional objects of this invention are the plasmids and expression vectors that contain said nucleic acid sequence that codes for the peptide of the invention, as well as prokaryotic or eukaryotic cells that express the peptide of the invention. A review of the principles of recombinant DNA technology may be found, for example, in the text book entitled "*Principles of Gene Manipulation: An Introduction to Genetic Engineering*," R. W. Old & S. B. Primrose, published by Blackwell Scientific Publications, 4$^{th}$ Edition (1989).

The peptide of the invention is able to at least partially inhibit neuronal exocytosis, probably through a mechanism that involves interfering with the assembly of the fusion protein complex (SNARE) and/or its thermal destabilization.

The neuronal-exocytosis (neurosecretion) inhibiting capabilities of the peptides of the invention became evident through a test that evaluates the strength of said peptides in inhibiting the release of catecholamines induced by calcium in chromaffin cells permeabilized with a detergent [see Example 1.2.1]. Briefly, the chromaffin cell cultures are incubated with epinephrine and norepinephrine containing tritium, are permeabilized with digitonin, and stimulated with calcium, and the amount of radioactivity released by the cells to the extracellular medium, which is a reflection of the exocytosis of said tritium-containing catecholamines, is measured.

The hexapeptide of the invention [SEQ. ID. No. 2], at a concentration of 1 mM, blocked approximately 20% of the release of catecholamines (epinephrine and norepinephrine) in permeabilized chromaffin cells, while the peptide with 13 amino acids [SEQ. ID. No. 3], at a concentration of 1 mM, inhibited approximately 35% of the release of catecholamines in the permeabilized chromaffin cells.

The peptides shown in SEQ. ID. No. 5 and SEQ. ID. No. 6, from the carboxyl end of SNAP-25 [SEQ. ID. No. 4], inhibited the secretion induced by $Ca^{2+}$ in chromaffin cells permeabilized with digitonin by approximately 40% when they were used at a concentration of 1 mM.

Parallel tests performed using; jointly, at least one peptide from the amino end of SNAP-25, for example, the peptide of SEQ. ID. No. 2 or of SEQ. ID. No. 3, and at least one peptide from the carboxyl end of SNAP-25, for example, the peptide of SEQ. ID. No. 5 or of SEQ. ID. No. 6, made it evident that the combined use of at least one peptide from the amino end of SNAP-25 and at least one peptide from the carboxyl end of SNAP-25 strengthens the biological activity observed for each of the peptides tested separately.

In one particular case, mixtures of peptides made up of one of the peptides shown in SEQ. ID. No. 2 or in SEQ. ID. No. 3 and one of the peptides shown in SEQ. ID. No. 5 or in SEQ. ID. No. 6, at a concentration of 0.5 mM for each of them, were tested, and an inhibition rate of 55% was obtained in the release of catecholamines in permeabilized chromaffin cells.

Taken all together, these results indicate that both types of peptides, both those from the amino end and those from the carboxyl end, inhibit catecholamine exocytosis, and that the combined use of peptides from the amino end and the carboxyl end strengthens the biological activity observed for each of them separately.

Therefore, the invention also provides a mix of peptides which includes:

(a) at least one peptide of the invention, and (b) at least one peptide with a sequence of 3 to 30 adjacent amino acids contained in SEQ. ID. No. 4 [henceforth, (COOH) peptide to indicate its relationship with the carboxyl end of SNAP-25].

In one particular embodiment, said mix of peptides is made up of at least one peptide selected from the group formed by the peptides shown in SEQ. ID. No. 2 and in SEQ. ID. No. 3, and at least one peptide selected from the group formed by the peptides shown in SEQ. ID. No. 5 and in SEQ. ID. No. 6.

The ability of the peptides of the invention to interfere with the formation and stability of the fusion complex (SNARE) became evident through the performance of in vitro reconstitution tests of the fusion protein complex with recombinant proteins [see Example 1.2.2]. Briefly, protein SNAP-25 was immobilized in 96-well plates, proteins VAMP and syntaxin were added in the presence and/or absence of the peptides of the invention, and the formation of the fusion protein complex (SNARE) was evaluated. The detection of the complex was performed using an antibody against syntaxin (anti-syntaxin), followed by a second, tagged antibody which recognizes the anti-syntaxin antibody. The data obtained seem to indicate that the presence of the peptides of the invention during the assembly of the fusion complex causes a significant decrease in same. Therefore, the mechanism of the neuronal exocytosis inhibiting action seems to imply that the peptides of the invention interfere with the formation and/or stability of the fusion protein complex (SNARE).

The results obtained with said tests suggest that the peptides of the invention, peptides which are small in size, between 3 and 30 amino acids, deriving from the amino acid sequence from the amino end of SNAP-25, along with (optionally) peptides from the carboxyl end of SNAP-25, act as neuronal exocytosis inhibitors. Given that these peptides imitate the sequences of neuronal proteins involved in exocytosis, their activity is specific, as they only interact with the corresponding neuronal proteins without affecting other cell components.

The action mechanism of the peptides of the invention seems to be similar to that of *botulinum* toxins, thus affecting the formation and/or stability of the fusion protein complex; so the peptides of the invention can be considered to have cosmetic/therapeutic applications similar to those described for *botulinum* toxin. Therefore, the peptides of the invention can become effective, stable, safe and economical substitutes for *botulinum* toxins, both in the treatment of facial wrinkles and/or asymmetry and in the treatment of the symptomatology of spastic diseases, and their use as neuroprotectors in the treatment of neurological disorders and neurodegenerative diseases.

The studies made by the applicants suggest, moreover, the innovative concept of the simultaneous use of peptides from the N-terminal and C-terminal domains of SNAP-25 as neuronal exocytosis modulators.

Taken together, the results obtained with the peptides of the invention, along with their stability and structural simplicity and the chemical diversity that can be obtained, keeping in mind the composition of the amino and carboxyl ends of SNAP-25, give the peptides of the invention great cosmetic and/or therapeutic potential.

The peptides of the invention may be used for pathological neuronal exocytosis-mediated cosmetic and/or therapeutic purposes.

Among the cosmetic applications of the peptides of the invention are the treatment and total or partial elimination of facial wrinkles and/or asymmetry in humans.

The invention provides a cosmetic composition that includes a cosmetically effective amount of at least one peptide of the invention, along with at least one cosmetically acceptable adjuvant. Additionally and optionally, said cosmetic composition may contain one of the peptides identified as (COOH) peptide.

For cosmetic applications, the peptides of the invention may be applied through any medium that produces contact between the peptide and the place where it is to act in a mammal's body, preferably in humans.

The cosmetically effective amount of peptide that should be applied, as well as the dosage for the treatment of facial wrinkles and/or asymmetry with the peptides and/or cosmetic compositions of the invention, will depend on numerous factors, including the age and condition of the person desiring treatment, the severity of the wrinkles and/or facial asymmetry, the method and frequency of application and the particular peptide to be used.

The presentation of the cosmetic compositions containing the peptides of the invention may be in any form that is suitable for application, e.g., solid, liquid or semi-solid, such as creams, ointments, gels or solutions, and the application of these compositions may be by any suitable means, preferably topically, so they will include the cosmetically acceptable adjuvants necessary to make up the desired form of administration. In a preferred and particular embodiment, the peptides of the invention are encapsulated in liposomes, along with (optionally) another or other (COOH) peptide(s), which are added to the other components of the cosmetic preparation. A review of the different cosmetic forms for applying active compounds and of the adjuvants necessary for obtaining same may be found, for example, in the text book "Cosmetologia de Harry" (Harry's Cosmetology), Wilkinson & Moore, Ed. Diaz de Santos (1990).

Therefore, an additional object of this invention is the use of the peptides of the invention in the preparation of cosmetic compositions for the treatment of facial wrinkles and/or asymmetry.

The invention also provides a method for the cosmetic treatment of facial wrinkles and/or asymmetry in mammals, preferably humans, which consists of applying a cosmetically effective amount of at least one peptide of the invention to the mammal that has facial wrinkles and/or asymmetry, along with (optionally) one or more (COOH) peptides, preferably in the form of a cosmetic composition containing it.

In addition, the peptides of the invention are suitable for the treatment of spastic diseases, for example, dystonias, strabismus, blepharospasm, facial scoliosis, tics, etc.; and/or as neuroprotectors in the treatment of neurological disorders and/or neurodegenerative diseases.

Among said neurological disorders are acute neurological diseases, for example, those that take place in the first stages of cerebral ischemia. It is a known fact that during an ischemic process an uncontrolled release of the neurotransmitter glutamate takes place in the affected area. This neurotransmitter interacts with specific neuronal membrane receptors causing a massive influx of calcium ions inside the neuron. The intracellular calcium causes the release of more glutamate, thus triggering a chain reaction. Moreover, the massive, prolonged influx of calcium inside the neurons causes their death, which translates into the formation of necrotic tissue in the ischemic zone. Clearly, the progress of the ischemic damage can be stopped, at least partially, if the uncontrolled glutamate exocytosis is controlled. Therefore, the peptides of the invention, because of their ability to inhibit exocytosis, may be suitable for preventing and/or slowing down the neuronal death that is characteristic of an ischemic process, and so would be useful in the treatment of neuropathologies that occur because of excessive glutamate exocytosis, such as, for example, senile dementia, Alzheimer's-related dementia, AIDS-related dementia, epilepsy, amiotrophic sclerosis, multiple/lateral sclerosis, etc. In this case, application in the treatment of neurological diseases would be similar to the one described for *botulinum* toxin A (18).

The peptides of the invention could therefore form part of a combined therapy (aimed at several therapeutic targets) with the objective of more effectively stopping neurodegeneration.

An additional object of this invention is a pharmaceutical composition which includes a therapeutically effective amount of at least one peptide of the invention, along with at least one pharmaceutically acceptable excipient. In one particular embodiment, said pharmaceutical composition also contains one or more (COOH) peptides. Alternatively, the pharmaceutical composition of the invention may contain a therapeutically effective amount of a vector that contains at least one nucleic acid sequence that codes for a peptide of the invention, along with at least one adjuvant and/or a pharmaceutically acceptable excipient. Said vector may be used in gene therapy.

The active products of the invention (peptides or vectors) may be administered for the treatment of pathological neuronal exocytosis, manifested, for example, by spastic diseases, neurological disorders or neurodegenerative diseases, through any medium that produces contact between the peptide and the place where it is to act in a mammal's body, preferably in humans.

The therapeutically effective amount of the active product of the invention [peptides or vectors (constructions)] that should be administered, as well as the dosage for the treatment of a pathological condition with the peptides and/or pharmaceutical compositions of the invention, will depend on numerous factors, including the age and condition of the patient, the severity of the disturbance or disorder, the method and frequency of administration and the particular peptide to be used.

The presentation of the pharmaceutical compositions that contain the peptides or vectors (constructions) of the invention may be in any form that is suitable for administration, e.g., solid, liquid or semi-solid, such as creams, ointments, gels or solutions, and these compositions may be administered by any suitable means, for example, orally, parenterally or topically, so they will include the pharmaceutically acceptable excipients necessary to make up the desired form of administration. A review of the different pharmaceutical forms for administering medicines and of the excipients necessary for obtaining same may be found, for example, in the "Tratado de Farmacia Galénica" (Treatise on Galenic Pharmacy), C. Fauli i Trillo, 1993, Luzán 5, S. A. Ediciones, Madrid.

As was previously mentioned, the peptides of the invention could form part of a combined therapy for the purpose of more effectively stopping neurodegeneration. In this case, the invention provides a pharmaceutical composition that includes at least one peptide of the invention, along with (optionally) another or other neuronal-exocytosis inhibiting compound(s), and along with at least one drug intended for another therapeutic target, selected from the group formed by a neuronal glutamate receptor blocker, a calcium chelator, an anti-oxidant, a free-radical destroyer and their combinations.

In one particular embodiment, said composition that is useful in combined therapy may contain at least one peptide of the invention, along with (optionally) another or other neuronal exocytosis inhibiting compound(s) and a neuronal glutamate receptor blocker. In another embodiment of this invention, said composition could contain at least one peptide of the invention, along with (optionally) another or other neuronal exocytosis inhibiting compound(s), a neuronal glutamate receptor blocker, a calcium chelator, an anti-oxidant and/or a free-radical destroyer. Among the neuronal exocytosis inhibiting compounds are peptides from the carboxyl end of SNAP-25, identified as (COOH) peptides. Many other examples of compositions may be proposed, all having in common the need to control neurotransmitter exocytosis.

An additional object of this invention is the use of the peptides of the invention or of vectors that contain at least one sequence that codes for a peptide of the invention, in the preparation of a medicine for the treatment of pathological neuronal exocytosis-mediated pathological diseases and/or disorders, such as, for example, spastic diseases, neurological disorders and/or neurodegenerative diseases.

In addition, the invention provides a method for the treatment in mammals of pathological neuronal exocytosis-mediated pathological diseases and disorders such as, for example, spastic diseases, neurological disorders and/or neurodegenerative diseases, which consists of administering to said mammal suffering from said pathological disease or disorder a therapeutically effective amount of at least one peptide of the invention, or of a vector containing at least one DNA sequence that codes for a peptide of the invention, preferably in the form of a pharmaceutical composition that contains it. In one particular embodiment of this invention, said pharmaceutical composition contains, in addition to the peptide or peptides of the invention, one or more (COOH) peptides.

The following examples serve to illustrate the nature of this invention and should not be considered in a restricting sense as regards said invention.

EXAMPLE 1

Neurotransmitter Exocytosis Inhibiting Peptides 1.1 Peptide Synthesis

The peptides shown in SEQ. ID. No. 2, SEQ. ID. No. 3, SEQ. ID. No. 5 and SEQ. ID. No. 6 have been synthesized through conventional methods for solid-phase chemical peptide synthesis using Fmoc and/or Boc-based synthetic methodology (16). The resulting peptides were purified by high-performance liquid chromatography (HPLC) and were analyzed by mass spectrometry.

1.2 Evaluation of Biological Activity

To evaluate the biological activity of the peptides obtained in Example 1.1, a test was developed that evaluates the strength of said peptides in inhibiting the release of catecholamines induced by calcium in chromaffin cells, as well as an in vitro reconstitution test of the fusion complex (SNARE).

1.2.1 Inhibition of the Release of Catecholamines

This test was performed to verify the neuronal exocytosis-inhibiting capabilities of the peptides synthesized in Example 1.1. In this test, the strength of said peptides is evaluated in inhibiting the release of catecholamines (norepinephrine and epinephrine) induced by calcium in chromaffin cells (obtained from suprarenal bovine glands) permeabilized with the detergent digitonin, in accordance with the method described by Gutiérrez el al. (1995 and 1997).

Briefly, the chromaffin cell cultures are incubated with [$^3$H]-epinephrine and [$^3$H]-norepinephrine, are permeabilized with 20 μM digitonin, and stimulated with calcium (10 μM), in the presence of the peptides to be tested (separate or mixed), and the amount of radioactivity released by the cells to the extracellular medium, which is a reflection of the exocytosis of [$^3$H]-epinephrine and [$^3$H]-norepinephrine, is measured.

The results obtained in inhibiting the release of catecholamines in permeabilized chromaffin cells were the following:

a) the peptide in SEQ. ID. No. 2, from the amino end of SNAP-25, at a concentration of 1 mM, blocked approximately 20% of the release of catecholamines in permeabilized chromaffin cells;

b) the peptide in SEQ. ID. No. 3, from the amino end of SNAP-25, at a concentration of 1 mM, inhibited approximately 35% of the release of catecholamines in the permeabilized chromaffin cells;

c) the peptides in SEQ. ID. No. 5 and SEQ. ID. No. 6, from the carboxyl end of SNAP-25, at a concentration of 1 mM, inhibited the secretion induced by $Ca^{2+}$ in chromaffin cells permeabilized with digitonin by approximately 40%; and d) mixtures of peptides made up of one of the peptides shown in SEQ. ID. No. 2 or in SEQ. ID. No. 3 and one of the peptides shown in SEQ. ID. No. 5 or in SEQ. ID. No. 6, at a concentration of 0.5 mM for each of them, inhibited the release of catecholamines in permeabilized chromaffin cells by approximately 55%.

Taken together, these results indicate that both types of peptides, both those from the amino end and those from the carboxyl end, inhibit catecholamine exocytosis, and that the combined use of peptides from the amino end and the carboxyl end strengthens the biological activity observed for each of them separately.

1.2.2 In Vitro Reconstitution

This test was performed to determine the ability of the peptides obtained in Example 1.1 to interfere with the formation and stability of the fusion complex (SNARE). The test consists of evaluating the in vitro reconstitution of the fusion protein complex with recombinant proteins produced in *Escherichia coli*. The reconstitution tests, based on ELISA (Enzyme-Linked Immuno Assay) methods, involve the immobilization of protein SNAP-25 in 96-well plates and the subsequent formation of the fusion protein complex by adding the proteins VAMP and syntaxin in the presence and/or absence of the peptides of the invention. The detection of the complex was performed using an antibody against protein syntaxin (anti-syntaxin), followed by an antibody which recognizes the anti-syntaxin antibody, covalently tagged with a peroxidase. The amount of fusion protein complex was tracked by adding 1,2-phenylenediamine dichloride, whose reaction with the peroxidase produces a product with an orangish-yellow color that absorbs 492 nm in an acid medium.

The data obtained show that the presence of the peptides obtained in Example 1.1 during the assembly of the fusion complex causes a significant decrease in same. Therefore, the mechanism of the action of said peptides seems to imply that said peptides interfere with the formation and/or stability of the fusion protein complex (SNARE).

BIBLIOGRAPHY

1. Schiavo, G., Rossetto, O. and Montecucco, C. Bases Moleculares del tétanos y del botulismo (Molecular bases of tetanus and botulism). *Investigación y Ciencia* 234. 46-55.
2. Montecucco, C. and Schiavo, G. (1994). Mechanism of action of tetanus and *botulinum* neurotoxins. *Mol. Microbiol.* 13, 1-8.
3. Schiavo, G., Rosetto, O., Benfenati, F., Poulain, B. and Montecucco, C. (1994). Tetanus and *botulinum* neurotoxins are zinc proteases specific for components of the neuroexocytosis apparatus. *Ann. NY Acad. Sci.* 710, 65-75.
4. Calakos, N. and Scheller, R. H. (1996). Synaptic vesicle biogenesis, docking and fusion: a molecular description. *Physiol. Rev.* 76, 1-29.
5. Sutton, R. B., Fasshauer, D., Jahn, R. and Brunger, A. T. (1998). Crystal structure of a SNARE complex involved in synaptic exocytosis at 2.4A resolution. *Nature* 395, 347-353.
6. Jankovic, J. and Brin, F. M. (1991). Therapeutic uses of *botulinum* toxin. *New Engl. J. Med.* 324, 1186-1194.
7. Jankovic, J. (1994). *botulinum* toxin in movement disorders. *Curr. Opin. Neurol.* 6, 358-366.
8. Jankovic, J. and Brin, M. F. (1997). *botulinum* toxin: historical perspective and potential new indications. *Muscle Nerve Suppl.* 6, S129-S145.

9. Davis, L. E. (1993). *botulinum* toxin-from poison to medicine. *West J. Med.* 128, 25-28.
10. Hughes, A. J. (1994). *botulinum* toxin in clinical practise. *Drugs* 48, 888-893.
11. Hambleton, P. (1992). *Clostridium botulinum* toxins: a general review of involvement in disease, structure, mode of action and preparation for clinical use. *J. Neurol.* 239, 16-20.
12. Borodic, G. E. and Pearces, L. B. (1994). New concepts in *botulinum* toxin therapy. *Drug Safety* 11, 145-152.
13. Brin, M. F., Blitzer, A., Stewart, C., Pine, Z., Borg-Stein, J., Miller, J., Nagalapura, N. S., and Rosenfeld, D. B. (1993). Disorders with excessive muscle contraction: Candidates for treatment with intramuscular *botulinum* toxin ("BoTox"). *Botulinum and Tetanus Neurotoxins* (Ed. B. R. DasGupata), 559-576.
14. Gutiérrez, L. M., Canaves, J., Ferrer-Montiel, A. V., Reig, J. A., Montal, M., and Viniegra, S. (1995). A peptide that mimics the carboxy terminal domain of SNAP-25 blocks $Ca^{2+}$ dependent exocytosis in chromaffin cells. *FEBS Lett* 372, 39-43.
15. Augine, G. J., Burns, M. E., DeBello, W. M. and Schweizer, F. E. (1996). Exocytosis: Proteins and perturbations. *Annu. Rev. Pharmacol. Toxicol.* 36, 659-701.
16. Pennington, M. W. and Dunn, B. N. (1994). Peptide synthesis protocols. Humana Press, Totowa.
17. Gutiérrez, L. M., Viniegra, S., Rueda, J., Ferrer-Montiel, A. V., Canaves, J. M. and Montal, M. (1997). A peptide that mimics the C-terminal sequence of SNAP-25 inhibits secretory vesicle docking in chromaffin cells. *J. Biol. Chem.* 272, 2634-2639.
18. Clarke, C. E. (1992). Therapeutic potential of *botulinum* toxin in neurological disorders. *Quart. J. Med.* 299, 197-205.

The invention claimed is:

1. A method of treating dystonia comprising administering to a subject in need of treatment a pharmaceutical composition comprising a therapeutically effective amount of a synthetic peptide whose complete amino acid sequence is selected from the amino acid sequence of SEQ ID NO:2 or the amino acid sequence of SEQ ID NO:3 and comprising a pharmaceutically acceptable excipient or an adjuvant or a mixture of a pharmaceutically acceptable excipient and an adjuvant to treat said dystonia.

2. The method according to claim 1, wherein the amino acid at the N-terminus of said peptide is acetylated.

3. The method according to claim 1, wherein the amino acid at the C-terminus of said peptide is amidated.

4. The method according to claim 1 wherein the administration of the pharmaceutical composition is a parenteral, an intranasal, an oral, or a topical administration.

5. A method of treating a condition mediated by pathological neuronal exocytosis selected from dystonias, blepharospasm, strabismus, facial scoliosis or tics, comprising administering to a subject in need of treatment a pharmaceutical composition comprising a therapeutically effective amount of a synthetic peptide whose complete amino acid sequence is selected from the amino acid sequence of SEQ ID NO:2 or the amino acid sequence of SEQ ID NO:3 and comprising a pharmaceutically acceptable excipient or an adjuvant or a mixture of a pharmaceutically acceptable excipient and an adjuvant to inhibit said pathological neuronal exocytosis.

6. A method of treating dystonia comprising administering to a subject in need of treatment a pharmaceutical composition comprising a therapeutically effective amount of a synthetic peptide whose complete amino acid sequence is selected from the amino acid sequence of SEQ ID NO:2 or the amino acid sequence of SEQ ID NO:3, wherein the amino acid residues of said peptides are D-amino acids, and comprising a pharmaceutically acceptable excipient or an adjuvant or a mixture of a pharmaceutically acceptable excipient and an adjuvant to treat said dystonia.

7. The method according to claim 6, wherein the amino acid at the N-terminus of said peptide is acetylated.

8. The method according to claim 6, wherein the amino acid at the C-terminus of said peptide is amidated.

9. The method according to claim 6, wherein the administration of the pharmaceutical composition is a parenteral, an intranasal, an oral, or a topical administration.

10. A method of treating a condition mediated by pathological neuronal exocytosis selected from dystonias, blepharospasm, strabismus, facial scoliosis or tics, comprising administering to a subject in need of treatment a pharmaceutical composition comprising a therapeutically effective amount of a synthetic peptide whose complete amino acid sequence is selected from the amino acid sequence of SEQ ID NO:2 or the amino acid sequence of SEQ ID NO:3, wherein the amino acid residues of said peptides are D-amino acids, and comprising a pharmaceutically acceptable excipient or an adjuvant or a mixture of a pharmaceutically acceptable excipient and an adjuvant to inhibit said pathological neuronal exocytosis.

* * * * *